US008821482B2

(12) United States Patent
Verhagen et al.

(10) Patent No.: US 8,821,482 B2
(45) Date of Patent: Sep. 2, 2014

(54) DEVICE AND METHOD FOR THE TREATMENT OF SKIN, AND USE OF THE DEVICE

(75) Inventors: Rieko Verhagen, Eindhoven (NL); Robbert Adrianus Maria Van Hal, Eindhoven (NL); Bart Gottenbos, Eindhoven (NL); Jozef Johannes Maria Janssen, Eindhoven (NL); Paul Anton Josef Ackermans, Eindhoven (NL); Francisco Morales Serrano, Eindhoven (NL); Sieglinde Neerken, Eindhoven (NL); Dirk Brokken, Eindhoven (NL); Guido Roosen, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 1490 days.

(21) Appl. No.: 12/305,438

(22) PCT Filed: Jun. 21, 2007

(86) PCT No.: PCT/IB2007/052399
§ 371 (c)(1),
(2), (4) Date: Oct. 27, 2009

(87) PCT Pub. No.: WO2008/001284
PCT Pub. Date: Jan. 3, 2008

(65) Prior Publication Data
US 2010/0063490 A1    Mar. 11, 2010

(30) Foreign Application Priority Data

Jun. 26, 2006    (EP) .................................... 06116057

(51) Int. Cl.
*A61B 18/18*    (2006.01)

(52) U.S. Cl.
USPC .................................. 606/9; 606/11; 606/17

(58) Field of Classification Search
USPC ..................................... 606/9, 11, 17
See application file for complete search history.

(56) References Cited

U.S. PATENT DOCUMENTS 5,586,981 A  *  12/1996  Hu ..................................... 606/9
5,620,478 A  *   4/1997  Eckhouse ....................... 607/88

(Continued)

FOREIGN PATENT DOCUMENTS

WO           0053261 A1      9/2000
WO        WO 00/53261    *  9/2000

(Continued)

OTHER PUBLICATIONS

Ute Jacobi et al: In vivo determination of skin surface topography using an optical 3D device, Skin Research and Technology Official Journal of International Society for Bioengineering and the Skin (ISBS) [and] International Society for Digital Imaging of Skin (ISDIS) [and] International Society for Skin Imaging (ISSI) vol. 10, No. 4, Nov. 2004, pp. 207-214, XP002467350 ISSN: 0909-752X.

*Primary Examiner* — Armando Rodriguez

(57) ABSTRACT

The invention provides a skin treatment device comprising a laser source (40) and focusing optics (50), such that a focal spot (18) is positioned in a dermis layer (24) of the skin to be treated. The laser beam (42) is powered and focused (16) such that a LIOB (laser induced optical breakdown) phenomenon is obtained, which affects the skin in order to stimulate re-growth of tissue. This in turn reduces wrinkles (30). The device may comprise wrinkle-determining means (52, 54, 56, 58). The focusing optics (50) may have a numerical aperture of at least 0.4. The invention also provides a corresponding method to treat skin, in particular to reduce wrinkles (30), by providing a focused laser beam (16) that causes LIOB in the dermis layer (24) of the skin. The advantage is that damage to overlaying epidermis layers may be avoided by the use of the very local LIOB phenomenon.

19 Claims, 2 Drawing Sheets

(56) References Cited

U.S. PATENT DOCUMENTS

| | | | |
|---|---|---|---|
| 5,735,844 A * | 4/1998 | Anderson et al. | 606/9 |
| 5,964,749 A | 10/1999 | Eckhouse et al. | |
| 6,032,071 A * | 2/2000 | Binder | 600/476 |
| 6,176,854 B1 * | 1/2001 | Cone | 606/15 |
| 6,482,199 B1 | 11/2002 | Neev | |
| 2001/0018603 A1 * | 8/2001 | Chess et al. | 607/104 |
| 2002/0125230 A1 | 9/2002 | Haight et al. | |
| 2003/0216719 A1 * | 11/2003 | Debenedictis et al. | 606/10 |
| 2004/0210275 A1 | 10/2004 | Town et al. | |
| 2005/0107852 A1 | 5/2005 | Levernier et al. | |
| 2006/0004306 A1 * | 1/2006 | Altshuler et al. | 601/3 |
| 2007/0239142 A1 * | 10/2007 | Altshuler et al. | 606/9 |
| 2011/0137230 A1 | 6/2011 | Altshuler | |

FOREIGN PATENT DOCUMENTS

| | | | |
|---|---|---|---|
| WO | 02053050 A1 | | 7/2002 |
| WO | 2004052181 A2 | | 6/2004 |
| WO | 2005011510 A1 | | 2/2005 |
| WO | WO 2005/011510 | * | 2/2005 |
| WO | WO2005011510 | * | 2/2005 |
| WO | 2006120635 A2 | | 11/2006 |

* cited by examiner

DEVICE AND METHOD FOR THE TREATMENT OF SKIN, AND USE OF THE DEVICE

FIELD OF THE INVENTION

The present invention relates generally to the treatment of skin using electromagnetic radiation. More particularly, the invention relates to a device and method for the treatment of skin, more particularly non-invasive wrinkle reduction of the skin. The invention furthermore relates to the use of a device in the treatment of skin.

BACKGROUND OF THE INVENTION

The desire to maintain a youthful appearance by preventing or reducing wrinkles in the skin is an important issue in human society. Many techniques have been designed to achieve the above goal. One of the techniques is to damage part of the dermis of the skin in order to induce the formation of connective tissue and new epidermis of the skin. Document U.S. Pat. No. 5,964,749 discloses a method and apparatus for wrinkle smoothing by applying pulsed light to the skin to heat and shrink collagen. In certain embodiments, light with a wavelength in the range of 600-1200 nm is applied, in the form of pulses, and with fluences of about 100 $J/cm^2$. Preferably, the epidermis is cooled.

A disadvantage of the disclosed method and the corresponding apparatus is that it has a high risk of damaging the epidermis, because all energy is provided non-discriminately. Damage to the epidermis is highly undesirable because this may lead to complications and health risks to the person being treated.

OBJECT OF THE INVENTION

An object of the invention is to provide a device and a method, as well as a use of the device, of the kind mentioned in the preamble, that are much safer to the person being treated in that damage to the epidermis is reduced or even substantially prevented.

SUMMARY OF THE INVENTION

The object is achieved according to the invention by means of a device comprising a laser source for generating a laser beam during a predetermined pulse time, and an optical system for focusing the laser beam into a focal spot, wherein a dimension of the focal spot and a power of the generated laser beam are such that, in the focal spot, the laser beam has a power density which is above a characteristic threshold value for skin tissue, above which value, for the predetermined pulse time, a laser induced optical breakdown (LIOB) phenomenon occurs in the skin tissue, and the optical system being arranged to set the focal spot, when the device is applied to the skin to be treated, to a treatment depth that corresponds to the dermis layer of the skin to be treated.

The device according to the invention is able to provide a laser induced optical breakdown (LIOB) phenomenon in the skin by providing sufficiently intense laser pulses. This LIOB is based on strong non-linear absorption of the laser light by the skin tissue, which occurs above a certain threshold value for the power density of the laser light. This strong absorption causes a very localized plasma that is able to damage or even remove tissue at the location of said plasma. This is caused by secondary, primarily mechanical effects such as rapid expansion of the generated plasma. This effect is very local, because below the threshold, there is zero or very little linear and non-linear absorption, while above the threshold a plasma is generated, which even more strongly absorbs the radiation. In other words, effects such as LIOB only occur at the focal spot, while above and below the focal spot no or very much weaker effects occur. This means that for example the epidermis may easily be safeguarded against undesired effects or damage. Another safety feature against damage to the epidermis is the fact that LIOB is very efficient. A very limited amount of energy is needed to obtain the desired local effects.

It is noted that the treatment depth may be fixed. The device will have a skin contact surface, with which the apparatus, in use, will be applied to the skin to be treated. Such a skin contact surface may comprise a laser beam exit window, or e.g. an aperture in a housing of the device. A window has the advantage that the position of the skin, and thus the dermis, can be more accurately defined with respect to the device. Hence the position of the focal spot may be determined accurately. In case the laser beam and the focal spot position are fixed, the focal spot may for example be present outside the device at the desired treatment depth.

It is noted that document WO 2005/011510 discloses a device for shortening hairs, which is based on the LIOB phenomenon. No skin treatment is suggested or disclosed. However, further details as to the general background of LIOB that are not disclosed in the present application may be found in this document.

In the present application, the expression "a dimension of the focal spot" may relate to any dimension of the focal spot on the basis of which the power density may be determined. In particular, the dimension may relate to the cross-sectional area or e.g. a diameter or waist of the laser beam.

In particular, the treatment depth is between 0.2 and 2 mm, more particularly between 0.5 and 1.5 mm, below a surface of the skin. This is based on a typical total thickness of the epidermis with the stratum corneum, in the face, of between 0.06 and 0.2 mm and a typical thickness of the dermis layer of 2 mm. Hence, the dermis may be found at a depth of between 0.2 and about 2 mm. A treatment depth of between 0.5 and 1.5 mm offers a range that allows treatment of the dermis with sufficient expansion yet without any risk for the surrounding layers such as the epidermis. In particular cases, the epidermis and/or dermis may be thinner or thicker, or may be present at a slightly different depth, such as on other parts of the body, e.g. hands. In that case, the skilled person will easily be able to determine the depth and/or thickness of the dermis, and adapt the device accordingly. A different treatment depth may then be fixed after establishing the depth and thickness of the dermis layer. It is also possible to use or include a device for automatic determination of the thickness of the dermis and/or epidermis, such as an ultrasonographic device, for example the Stiefel Cutech "Dermal depth Detector", or alternatively an OCT device (optical coherence tomography).

In a special embodiment, the device further comprises a skin surface image sensor, that is arranged to determine topographical information of the surface of the skin to be treated. In particular, the sensor is arranged to determine curvature and/or a height map of the skin to be treated with respect to the device. Examples of such sensors are known per se, but special mention is made of a sensor system comprising a projector arranged to project a pattern on the skin surface and a sensor that is arranged to detect the image of the pattern on the skin, and to determine the desired topographical information from the detected image. Among the alternative possibilities is also contemplated a system of two or more cameras, such as ccd cameras, that may be provided with a control unit that is able to derive (3D) topographical information from the respective camera images.

In a special embodiment, the skin surface image sensor is arranged to determine a position of a line of a locally deepest depression of the skin. Such a line of a locally deepest depression corresponds to a wrinkle. There may be more than one such line at a time in one image, and two or more lines may be interconnected. The skin surface image sensor comprises e.g. a control unit that is arranged to determine said position, for example based on the strongest bends in the projected pattern, the deepest shadow, or on any other technique known to the skilled person. Such embodiment helps in finding a correct position for treatment. This may e.g. be indicated by an audible or visual signal etc.

In a special embodiment, the device further comprises a display for displaying the topographic information. This may be in the form of a map or other visual display of an image of the skin, or of the wrinkles only. It is also possible to indicate the momentary position of the laser beam, or, if emitted, the projected position thereof. The operator may then manually position the device for an appropriate treatment, according to the displayed information.

In a particular embodiment, the optical system is adjustable, based on the topographical information, such that the focal spot is deliverable at the treatment depth. By virtue of this feature, it is for example possible to take into account that the dermis in a wrinkle may be present somewhat deeper than in the surrounding skin. Such a difference may be encountered when the skin cannot be smoothed completely by a laser beam exit window or the like.

In particular, the optical system comprises an adjustable lens or an adjustable mirror. Both elements, or a combination thereof, can provide the focusing action. Both may be made adjustable to adjust the position of the focal spot, both in depth with respect to the skin surface and in position across the skin surface. The adjustable lens may comprise a lens with a distance setting, or may be a zoom lens. The adjustable mirror may comprise a mirror that is rotatable in one or more, preferably two, directions. The mirror may be flat, e.g. when combined with a lens, or may be concave, in particular if the mirror provides focusing action.

Advantageously, the adjustable lens comprises an autofocus lens. Such a lens is automatically adjusted with respect to the skin surface. This ensures a correct treatment depth in almost all circumstances.

In a special embodiment, the optical system further comprises a laser beam manipulator for positioning the focal spot. Such a laser beam manipulator may comprise for example a moveable mirror and a mirror actuator for moving the mirror, as well as a control unit therefor. The laser beam manipulator may also comprise the adjustable lens or mirror. The laser beam manipulator may be used for positioning the focal spot on and in the skin. The operator may control the laser beam manipulator, e.g., on the basis of displayed topographical information on the skin.

In a particular embodiment, the laser beam manipulator is arranged to position the focal spot with respect to the line of a locally deepest depression, and in particular on said line, of course within the dermis. For this purpose, a control unit may appropriately control the laser beam manipulator on the basis of position information of said line, for example based on topographical information about the skin surface. This embodiment is very easy and safe to use, especially for home-use. A user can apply the apparatus to the skin. The image sensor determines topographical information, which is evaluated, e.g., by the sensor or the control unit. The control unit then controls the laser beam manipulator to direct one or more laser beam pulses to be emitted in the appropriate direction(s). As soon as the device has finished the treatment, a signal may be given.

The invention as a whole uses the circumstance that the skin transmits electromagnetic radiation that is to be focused in the dermis, in a very small focal spot. To maximize this effect, a wavelength of the laser beam is between 800 and 1100 nm. In this range, transmission is high and scattering and linear absorption are low. Thus, LIOB may be achieved easily, accurately (i.e. very locally) and efficiently. It is however not excluded to use other wavelengths.

In particular, the predetermined pulse time is between 100 ps and 10 ns. In this range, the plasma generated by the LIOB is very local, i.e. has a small spatial extension, which minimizes the risk of unintended damage to surrounding tissues. Furthermore, the peak power required to obtain LIOB is substantially independent of the pulse time in this range. However, other pulse times, e.g. in the range of about 100 fs to 100 ps, may also be used.

In a special embodiment, a deliverable energy level in the laser beam pulse is between 0.1 and 10 mJ, measured at the surface of the skin. Such energy levels have turned out to be useful in the treatment, i.e. generating sufficient damage to stimulate new tissue growth. More specifically, the energy level is between about 0.5 and 5 mJ, and typically about 1 mJ. Note, however, that other energy levels are not excluded, such as levels up to about 20 mJ for large treatment depths of up to 2 mm. In the above energy level indications, the energy is measured at the surface of the skin, i.e. it relates to the energy actually emitted into the skin.

In a special embodiment, a deliverable energy level in the laser beam pulse is between 0.1 and 5 mJ, measured in a plasma generated by the LIOB phenomenon. In particular, said energy level is between about 0.5 and 5 mJ, typically about 1 mJ. These energy levels are measured, or estimated, to be actually involved in the plasma of the LIOB phenomenon.

In all of the above, it is to be understood that instead of a single pulse, it is also possible to provide a number of pulses, as long as the pulses generate a LIOB phenomenon.

In a particular embodiment, the optical system has a numerical aperture of at least 0.2, preferably at least 0.4, more preferably at least 0.6. Such values for the numerical aperture relate to safety for the overlying skin layers, in particular the epidermis. Since, in particular, the epidermis contains many chromophores such as melanin, the residual linear absorption in the epidermis is not negligible. Hence, it is advantageous to keep the fluence, or energy density, in such layers sufficiently low. This may be achieved by providing a strongly focused laser beam, i.e. with a large angle of convergence, and hence with a large numerical aperture of the optical system. The laser beam then covers a sufficiently large area to maintain the fluence in the epidermis within an acceptable range. In particular, the fluence in the epidermis should be at most 3 J/cm2. Note that the numerical aperture depends on the treatment depth and on the actual energy in the pulse. Model calculations show that a numerical aperture of at least 0.4 suffices for a treatment depth of 0.5 mm and an energy of 1 mJ in the plasma (in the focus area), while higher NAs are needed for higher energy levels and smaller treatment depths, and vice versa.

The invention also relates to a method of treating skin, in particular non-invasive treatment of skin tissue, comprising providing a laser beam having a laser power during a predetermined pulse time, focusing said laser beam into a focal spot with a dimension, such that, in the focal spot, the laser beam has a power density which is above a characteristic threshold value for skin tissue, above which value, for the predetermined pulse time, a laser induced optical breakdown (LIOB) phenomenon occurs in the skin tissue, characterized in that the focal spot is positioned in a dermis layer of the skin. Such a cosmetic treatment is desirable for e.g. people who wish to reduce wrinkles in the skin. The mechanism has been elucidated in the discussion of the device according to the invention, and is hence not repeated here. Specific technical features may then also be used in the method according to the invention, unless they specifically relate to the device. Not all such features will be repeated below, although the combinations are deemed explicitly disclosed. It is furthermore stressed that the method provides a way of dealing with wrinkles in a safe way, that may be used by non-professional users in a safe and convenient way.

In particular, the focal spot is positioned at a depth of between 0.2 and 2 mm below the surface of the skin, in particular between 0.5 and 1.5 mm, in order to be in the dermis, with a safety margin to prevent undesired damage of other skin tissue.

Preferably, a delivered energy level in the laser beam pulse is between 0.1 and mJ, measured in a plasma generated by the LIOB phenomenon. This energy level is measured or at least estimated at the location of the focal spot.

In particular, a fluence of the laser beam pulse is at the most 3 J/cm2 in the skin between the surface of the skin and the dermis layer. Such a fluence is deemed safe for said skin layers. Together with the preferred energy levels for the laser beam pulse, this leads to preferred laser beam apical angles, in particular of at least 11° (half angle) for 1 mJ and a treatment depth of 0.5 mm. In dependence on the desired treatment depth and pulse energy, the skilled person can easily determine the preferred apical angle, or the related numerical aperture, preferably with the help of the graph of FIG. 2.

In a special embodiment, the method further comprises a step of providing a substance between the skin to be treated and the device, said substance having a refractive index of between about 1.3 and 1.6, in particular about 1.4. Such an index-matching substance helps to prevent optical bending effects by the skin, both macroscopically by the curvature at a wrinkle, but also microscopically by the surface structure of the skin itself. It furthermore reduces losses due to reflection at the interfaces.

The invention also relates to the use of a device according to the invention in the treatment of skin, in particular non-invasive wrinkle reduction in the skin. This aspect uses the advantage that LIOB has in treating skin, i.e. it can provide small amounts of energy very locally, and at a desired depth without affecting the layers above. The use is thus inherently safe in particular in comparison to other treatments that apply electromagnetic radiation.

DETAILED DESCRIPTION OF EXAMPLES

Figure 1:
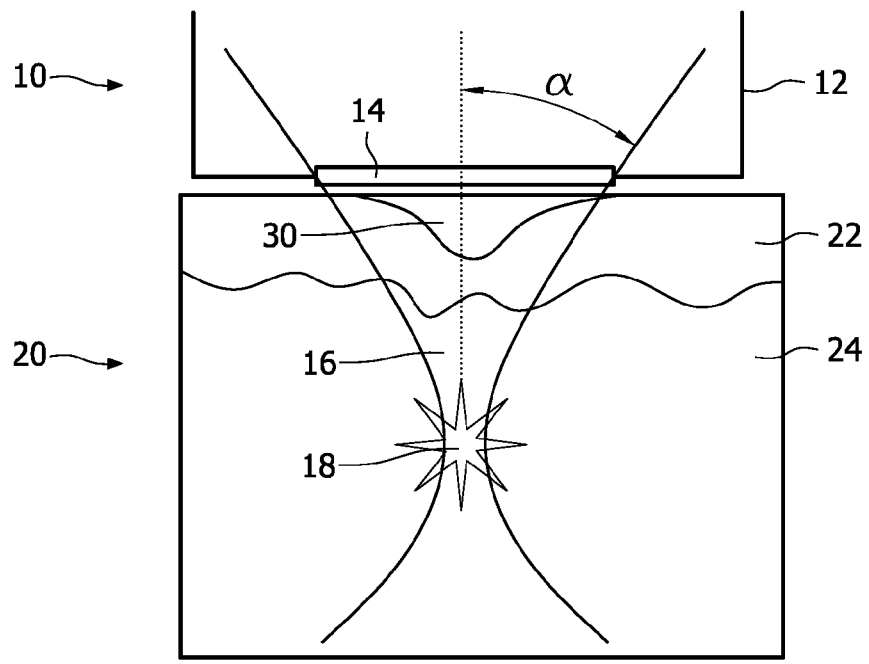
FIG. 1 diagrammatically shows the most important parts of the device in use when treating skin.

FIG. 1 diagrammatically shows the most important parts of the device in use when treating skin. By means of reference numeral 10, a part of the device is designated, while 20 designates skin to be treated. The device 10 comprises a housing 12 with a laser beam exit window 14, through which a laser beam 16 is emitted that is focused in a focal spot 18.

The skin 20 comprises an epidermis 22 and a dermis 24. The skin 20 has a wrinkle 30, which is filled with an index-matching medium.

In use, the device 10, or at least the part shown here, is applied to the skin 20. A laser beam 16 is emitted through the laser beam exit window 14, which may be made of a transparent material or may simply be an aperture in the housing 12. However, a window of a transparent material has the advantage that it better defines the position of the skin 20 with respect to the device 10.

The laser beam 16 roughly resembles a hyperboloid with an apical angle $\alpha$ and a waist or focal spot 18. The focal spot is also the position of the LIOB phenomenon, indicated by means of the explosion symbol. The convergence of the laser beam into a focal spot helps localize the LIOB phenomenon and helps prevent damage to the epidermis 22, because there the power density is much lower than in the focal spot 18 in the dermis 24.

The focal spot 18 is positioned below the wrinkle 30 and in the dermis 24. To prevent a lens effect by the skin and the curvature of the wrinkle 30, an index-matching material is applied to the skin in order to fill the wrinkle between the epidermis 22 and the window 14. The index-matching material should have an index of refraction approximately between the index of refraction of the window 14 and that of the epidermis 22, preferably approximately equal to the refractive index of the epidermis 22. In the ideal case, the window 14 and the index-matching material have the same index of refraction as the epidermis, roughly 1.4.

Figure 2:
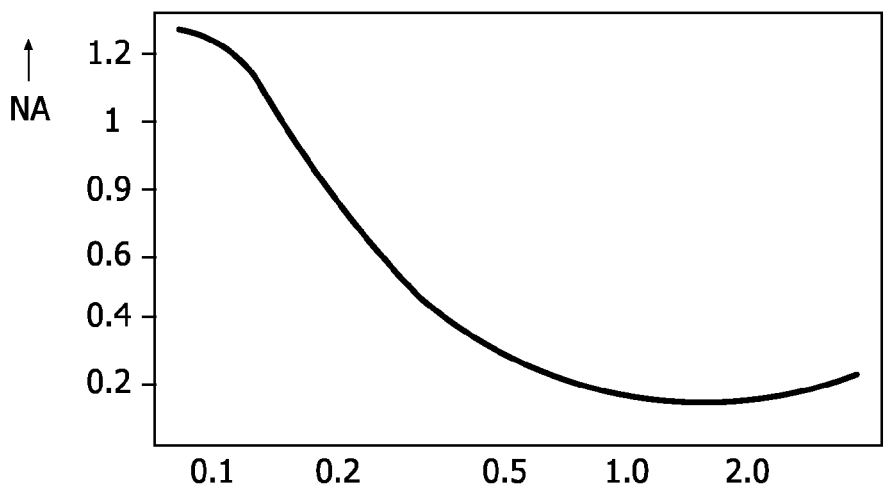
FIG. 2 shows a model graph of minimum NA as a function of treatment depth, FIG. 3 diagrammatically shows an embodiment of the device according to the invention, and FIG. 4 diagrammatically shows an exemplary image pattern on a wrinkled skin.

FIG. 2 shows a graph of a model calculation of the minimum numerical aperture (NA) needed to generate a laser-induced optical breakdown phenomenon by applying 1 mJ of energy in the plasma in the focus area without causing harm to the epidermal layers above, as a function of treatment depth below the skin surface. For example, the NA of the optical system needed to achieve LIOB at 0.5 mm below the skin surface with 1 mJ is about 0.4. In order to have a safe margin to prevent damage to the epidermal layers, the NA should thus be at least 0.4. Note that the NA needed for large treatment depths is of course smaller than that for small treatment depths, because of the larger distance to the epidermal layers that are not to be damaged. However, the total intensity and energy needed to achieve a sufficient LIOB plasma formation at the treatment depth becomes larger, due to residual absorption and scattering in the overlaying layers.

The above calculation and graph hold for a typical energy of 1 mJ. In the case of higher energies, the graph will shift to higher values of NA, while for lower energies the minimum NA will become smaller.

Figure 3:
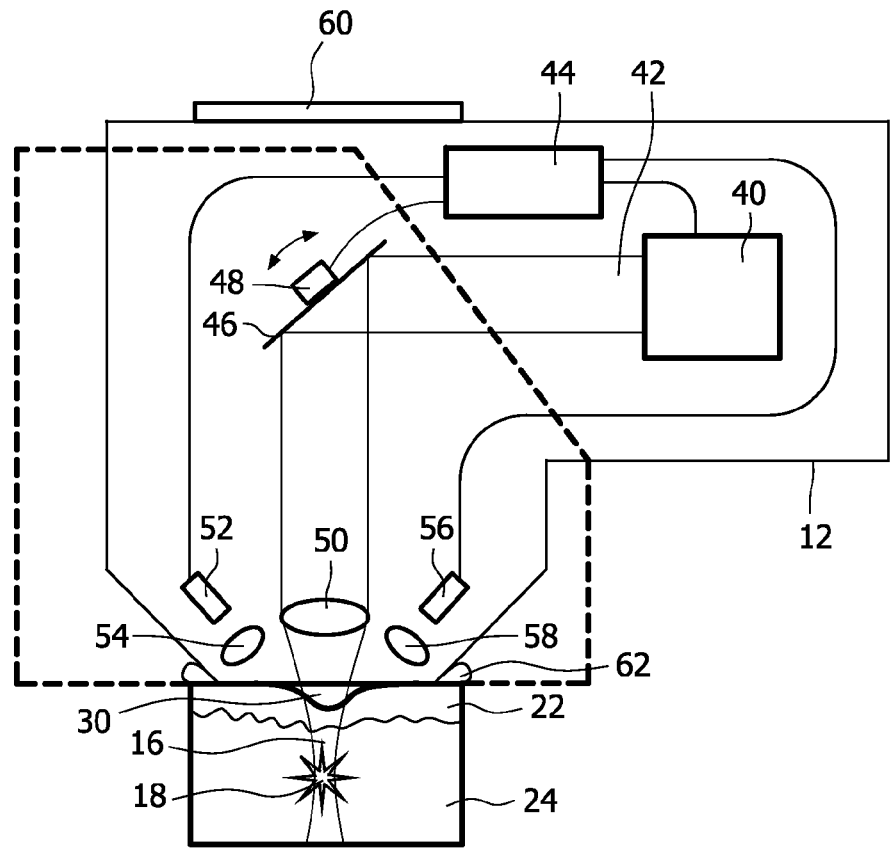

FIG. 3 diagrammatically shows an embodiment of the device according to the invention. In this Figure, as well as in any other Figures, similar parts are denoted by the same reference numerals.

The device comprises a housing 12 with a laser source 40 that emits an unfocused laser beam 42, and is connected to control unit 44 that also controls laser beam manipulator 48 with a mirror 46. Optical system 50 focuses the unfocused laser beam 42 into a focused laser beam 16 with a focal spot 18.

A fringe projector and fringe projection optics have been designated 52 and 54, respectively, while a wrinkle image sensor and wrinkle imaging optics have been denoted 56 and 58, respectively.

Reference numeral 60 denotes display means, while 62 denotes an index-matching medium.

It is noted that the parts within the dashed box may be provided so as to be connected to the laser source 40 by means of e.g. an optical fiber. This provides a small and lightweight applicator unit, with the bulkier and heavier laser source etc., in a separate and stationary unit.

The control unit 44 controls laser source 40 to emit laser radiation in an unfocused beam 42. This may be done in a pulsed way with a predetermined pulse time, for example between 0.1 and 100 nanoseconds, other pulse times not being ruled out. The beam may be focused by means of the optical system 50, here indicated only very diagrammatically by means of a single lens. This lens 50 may also be a complex lens, and may preferably be a zoom lens. A zoom lens may have a variable focal length or may be a lens with an adjustable position. In all cases, the position of the focal spot 18 with respect to the skin may be adjusted.

Furthermore, the mirror 46, which may be manipulated by laser beam manipulator 48, which in turn is controlled by control unit 44, is arranged to position the focal spot 18 with respect to the skin, in particular with respect to a wrinkle 30.

The position of such a wrinkle 30 may be determined as follows. Fringe projector 52 projects a pattern of one or more fringes onto the skin via fringe projection optics 54. The pattern, as present on the skin with wrinkles, is imaged by wrinkle imaging sensor 56 via wrinkle imaging optics 58. The image thus sensed is evaluated by the control unit 44 by means of (software) methods known in the art. In this way, topographic information on the skin, in particular the height as a function of the position on the skin, is obtained. On the basis of this information, the control unit 44 controls the laser beam manipulator 48 to direct the focal spot 18 to a position below the wrinkle 30.

Note that it is also possible to obtain the information in other ways. For example, both parts 52 and 56 may be cameras with corresponding optics 54 and 58. Both cameras obtain pictures of the skin surface, which by means of known imaging software may be converted to 3D surface maps.

The device described above is easily automated, in that on application of the device to the skin, a surface map of the skin may be made. On the basis of any wrinkles detected in said surface map, the control unit 44 aims laser beam pulses at the dermis under said wrinkles. After treating all or a selected number of the wrinkles, a signal may be given, which indicates that the treatment has been completed. No operator is required to perform the treatment, determine the wrinkles, et cetera. Such a device is well-suited for consumer use.

The information, or an image of the skin that will be treated, may also be displayed on the display 60. This offers the possibility of a visual check before actually treating the skin. It also offers the possibility to use a device with a fixed position of the focal spot, i.e. without a laser beam manipulator and/or without a zoom lens. For example, if the focal spot is arranged at a fixed depth of 1.5 mm, as well as in a fixed position with respect to the device, which may be indicated in the display by a cross or the like, an operator may manually position the device on top of a wrinkle. He then applies the required amount of laser energy, after which a new treatment spot may be selected.

Figure 4:
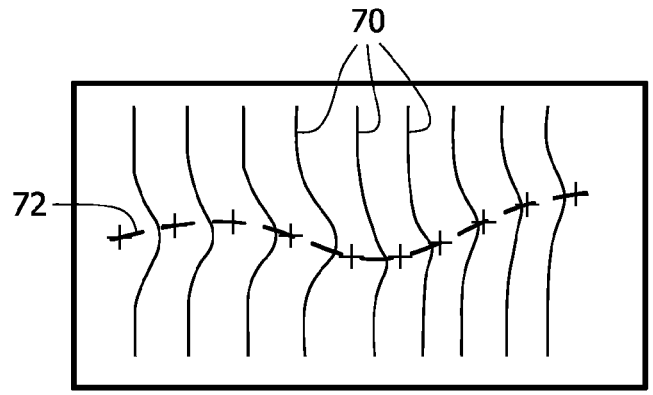

FIG. 4 diagrammatically shows an exemplary line pattern of alternating dark lines 70 and bright lines on the skin, which are the result of projecting a pattern of parallel lines on a skin with a wrinkle. The wrinkle is clearly visible as a valley, indicated by the dashed line 72. A typical treatment protocol, in the form of spots to be irradiated by the laser, has been indicated by a series of crosses. Obviously, any spot on or close to the dashed line may be selected to treat the wrinkle.

The invention as disclosed herein is not deemed limited to the described embodiments. Rather, since the skilled person may adapt and modify such embodiments within his art, the scope of the invention is determined by the appended claims.

The invention claimed is:

1. A device for non-invasive treatment of skin tissue comprising:
    a laser source for generating a laser beam during a predetermined pulse time,
    a skin surface image sensor for determining topographical information about a surface of the skin above the tissue in a dermis layer to be treated, wherein the skin surface image sensor is arranged to determine a position of a line of a locally deepest depression of the skin tissue; and
    an optical system for focusing the laser beam into a focal spot, with respect to the line of the locally deepest depression of the skin tissue,
where, in operation:
    The optical system positions the focal spot at a treatment depth within the dermis layer of the skin tissue; and
    the optical system dimensions the focal spot and the laser source powers the laser beam such that, in the focal spot, the laser beam has a power density which is above a characteristic threshold value for skin tissue, above which value, for the predetermined pulse time, a laser induced optical breakdown (LIOB) phenomenon occurs in the skin tissue.

2. A device according to claim 1 where the treatment depth is between 0.2 and 2 mm below a surface of the skin tissue.

3. A device according to claim 2 where the treatment depth is between 0.5 and 1.5 mm below the surface of the skin tissue.

4. a device according to claim 1 where the optical system is adjustable based on the topographical information.

5. A device according to claim 1 where the optical system comprises a laser beam manipulator for positioning the focal spot.

6. A device according to claim 1 where the optical system comprises a laser beam manipulator for positioning the focal spot below said deepest depression of the skin tissue.

7. A device according to claim 1 where a wavelength of the laser beam is within a range from 800 to 1100 nm.

8. A device according to claim 1 where the predetermined pulse time is within a range from 100 ps to 10 ns.

9. A device according to claim 1 where a deliverable energy level in the laser beam pulse is within a range from 0.1 to 10 mJ, measured at a surface of the skin tissue.

10. A device according to claim 1 where a deliverable energy level in the laser beam pulse is within a range from 0.1 to 5 mJ, measured in a plasma generated by the LIOB phenomenon.

11. A device according to claim 1 where a fluence of the laser beam pulse is at most 3 $J/cm^2$ in an epidermis area through which said laser beam passes to reach said derails layer.

12. A device according to claim 1 where the optical system has a numerical aperture of at least 0.2.

13. A method for utilizing a device for non-invasive treatment of skin tissue comprising:
    providing a laser beam having a predetermined laser power during a predetermined pulse time,
    determining topographical information about a surface of the skin above the tissue in a dermis layer to be treated, determining from said topographical information a position of a line of a locally deepest depression of the skin tissue;

focusing said laser beam into a focal spot within the dermis layer of the skin tissue with respect to the line of the locally deepest depression of the skin tissue, and having a dimension such that, in the focal spot, the laser beam has a power density which is above a characteristic threshold value for skin tissue, above which value, for the predetermined pulse time, a laser induced optical breakdown (LIOB) phenomenon occurs in the skin tissue.

14. A method according to claim 13 comprising a step of providing a substance between the skin tissue to be treated and the device, said substance having a refractive index within a range of about 1.3 to 1.6.

15. A device according to claim 1 where the non-invasive treatment of skin a tissue comprises wrinkle reduction.

16. A device according to claim 9 where the deliverable energy level in the laser beam pulse is about 1 mJ, measured at a surface of the skin tissue.

17. A device according to claim 1 where the optical system has a numerical aperture of at least 0.4.

18. A device according to claim 1 where the optical system has a numerical aperture of at least 0.6.

19. A method according to claim 14 where said substance has a refractive index of about 1.4.

\* \* \* \* \*